(12) United States Patent
Egan et al.

(10) Patent No.: US 6,458,759 B1
(45) Date of Patent: Oct. 1, 2002

(54) COMPOSITIONS AND METHODS FOR ISOLATING LUNG SURFACTANT HYDROPHOBIC PROTEINS SP-B AND SP-C

(75) Inventors: Edmund A. Egan, Amherst; Lynn M. Hlavaty, Derby; Bruce A. Holm, Batavia, all of NY (US)

(73) Assignee: Ony, Inc., Amherst, NY (US)

( * ) Notice: Subject to any disclaimer, the term of this patent is extended or adjusted under 35 U.S.C. 154(b) by 0 days.

(21) Appl. No.: 09/435,204

(22) Filed: Nov. 5, 1999

Related U.S. Application Data

(62) Division of application No. 08/845,422, filed on Apr. 25, 1997.
(60) Provisional application No. 60/016,305, filed on Apr. 26, 1996.

(51) Int. Cl.⁷ .................. A01N 37/18; A61K 38/00; C07K 5/00; C07K 7/00

(52) U.S. Cl. ................. 514/2; 514/12; 530/300; 530/324; 424/185.1
(58) Field of Search ................ 514/2, 12; 530/300, 530/324; 424/185.1

(56) References Cited

U.S. PATENT DOCUMENTS

| | | | | | |
|---|---|---|---|---|---|
| 4,918,161 | A | * | 4/1990 | Steinbrink et al. | 530/300 |
| 5,238,920 | A | * | 8/1993 | Sarin et al. | 514/12 |
| 5,302,581 | A | * | 4/1994 | Sarin et al. | 514/12 |
| 5,547,937 | A | * | 8/1996 | Dhaon | 514/12 |
| 6,020,307 | A | * | 2/2000 | Egan et al. | 514/2 |

* cited by examiner

Primary Examiner—Avis M. Davenport
(74) Attorney, Agent, or Firm—Ropes & Gray

(57) ABSTRACT

The present invention describes compositions of biologically active surfactant proteins SP-B and SP-C of high purity and high-yield methods for isolating SP-B and SP-C.

22 Claims, 2 Drawing Sheets

COMPOSITIONS AND METHODS FOR ISOLATING LUNG SURFACTANT HYDROPHOBIC PROTEINS SP-B AND SP-C

This application is a divisional of application Ser. No. 08/845,422 filed Apr. 25, 1997, which application is based on Provisional Application Ser. No. 60/016,305 filed Apr. 26, 1996.

FIELD OF THE INVENTION

The invention relates to (1) a composition of matter in which the polypeptide has the chemical structure, biophysical activity and physiologic effects of the small, hydrophobic protein SP-B with a purity of ≧95%; (2) a second composition of matter in which the polypeptide solute has the chemical structure, biophysical activity and physiologic effects of the small, hydrophobic protein SP-C with a purity of ≧95%; and (3) the methods for producing the compositions of matter.

BACKGROUND OF THE INVENTION

Role of Surfactant in Pulmonary Physiology

Inhaled air containing oxygen travels through the trachea, the bronchi, and the bronchioles to the hundreds of millions of terminal alveoli. The terminal alveoli are the air spaces in the lungs where oxygen is taken up by the blood in exchange for carbon dioxide.

At the interface between the gas in the terminal alveoli and the liquid of the lung tissue, (i) oxygen diffuses into the blood from the alveoli and (ii) carbon dioxide diffuses from the blood to the alveolar air before being exhaled. To diffuse from the alveolar gas to the blood, an oxygen molecule must traverse the liquid lining the alveoli, at least one epithelial cell, the basement membrane, and at least one endothelial cell.

Pulmonary surfactant acts at the interface between alveolar gas and the liquid film lining the luminal surface of the cells of the terminal alveoli. The normal pulmonary surfactant lining is extremely thin, usually no more than 50 nm thick. Thus, the total fluid layer covering the 70 square meters of alveolar surface in an adult human is only approximately 35 ml.

For materials to be effective lung surfactants, surfactant molecules must move rapidly to the surface of the liquid. Pulmonary surfactant functions by adsorbing to the surface of the liquid covering these lining cells and changing surface tension of the alveolar fluid during the respiratory cycle.

Surface tension is a characteristic of most liquid solutions. At the interface between liquid and a gas phase, the movement of molecules at the surface of the liquid is restricted by intermolecular forces acting on those molecules. The intermolecular forces have a net direction that tends to decrease the area of the surface. The net force at the surface is referred to as surface tension. Surface tension varies with molarity, temperature and multiple solutes. Surface tension has units of force per unit length (dynes/cm or mN/m). The vector of the surface tension force is perpendicular to the plane of the interface.

The lungs of vertebrates contain surfactant, a complex mixture of lipids and protein which causes surface tensions to rise during surface expansion (inflation) and decrease during surface compression (deflation). During lung deflation, surfactant decreases surface tension to ≦1 mN/m, so that there are no surface forces that would otherwise promote alveolar collapse. Aerated alveoli that have not collapsed during expiration permit continuous $O_2$ and $CO_2$ transport between blood and alveolar gas and require much less force to inflate during the subsequent inspiration.

In order to attain sufficient uptake of oxygen by the blood and excretion of carbon dioxide from the blood, an animal's lungs must ventilate the terminal alveoli simultaneously and evenly. Either unsynchronized or uneven ventilation will prevent sufficient oxygen uptake into the circulating blood and result in the retention of carbon dioxide in the body.

During inflation, lung surfactant increases surface tension as the alveolar surface area increases. A rising surface tension in expanding alveoli opposes over-inflation in those airspaces and tends to divert inspired air to less well-aerated alveoli, thereby facilitating even lung aeration.

Surfactant Deficiency or Dysfunction

Although the exact composition and physical characteristics of natural lung surfactant have not been determined, material isolated from the lumen of lungs, termed natural surfactant, contains a mixture of phospholipids, neutral lipids, and proteins. (Jobe A, Ikegami M, Surfactant for the treatment of respiratory distress syndrome. Am Rev Respir Dis, 1987; 136:1256–75.) The phospholipids are not specific to surfactant, but are also present in other biologic materials, particularly membranes. The predominant phospholipids in surfactant, however, are disaturated phosphatidylcholines which are present in low concentrations in most membranes. Among the proteins found in the lung lumen are mucoproteins, plasma proteins, and lung specific proteins. These lung specific proteins are described in more detail in Section 2.3.

The alveoli are lined with epithelial cells that have a role in producing surfactant, maintaining the activity of surfactant, and preventing the inactivation of surfactant. The epithelial cells form a continuous, tight barrier that normally prevents entry into the alveoli of molecules from the circulation that can inhibit surfactant.

The alveolar epithelium consists of at least two types of alveolar cells, referred to as type I and type II alveolar cells. The type II alveolar cells normally synthesize both the phospholipids and proteins that are in lung surfactant, store newly synthesized material in the intracellular inclusion bodies, secrete the surfactant into the alveolar space, absorb surfactant from the alveolar space, and metabolize material re-incorporated into the type II cell. The role of type I cells in surfactant function has not yet been identified.

Lung surfactant is normally synthesized at a very low rate until the last six weeks of fetal life. Human infants born more than six weeks before the normal term of a pregnancy have a high risk of being born with inadequate amounts of lung surfactant and inadequate rates of surfactant synthesis. The more prematurely an infant is born, the more severe the surfactant deficiency is likely to be. Severe surfactant deficiency can lead to respiratory failure within a few minutes or hours of birth. The surfactant deficiency produces progressive collapse of alveoli (atelectasis) because of the decreasing ability of the lung to expand despite maximum inspiratory effort. As a result, inadequate amounts of oxygen reach the infant's blood.

Endogenous surfactant production typically accelerates after birth, even in quite premature infants. If the infant survives the first few days, lung surfactant status generally becomes adequate.

Additional causes of respiratory failure from surfactant dysfunction have been reported due to defects in surfactant synthesis (congenital protein B deficiency), or in secretion or metabolism of surfactant (alveolar proteinosis). In addition, lung surfactant can be inhibited and inactivated in vitro by a variety of proteins, cell wall phospholipids, enzymes, and other products of inflammatory responses.

Injury to juvenile and adult animals can also inactivate surfactant and produce a respiratory failure with a similar pathophysiology to the surfactant deficiency in premature infants. This respiratory failure is often referred to as the Adult (or Acute) Respiratory Distress Syndrome, ARDS. This syndrome results from several simultaneous pathologic processes, one of which is generalized inhibition of the extra-cellular surfactant in the alveolar space plus dysfunction of the type II alveolar cells which adversely affect the synthesis, secretion, or metabolism of surfactant.

Current treatment of respiratory failure includes supplementation of oxygen, mechanical ventilation, and instillation or aerosolization of materials with lung surfactant activity. Some patients die from respiratory failure despite current treatments, some survive with permanently damaged lungs, and other patients recover after prolonged therapy.

Hydrophobic Surfactant Proteins

Lung surfactants are complex materials composed of multiple molecules that interact physically, without combining chemically, to achieve their biologic activity. Natural lung surfactant contains lipids and proteins. There are two types of lung surfactant proteins, hydrophilic and hydrophobic. The two hydrophilic surfactant proteins identified to date, named SP-A and SP-D, are water soluble, chloroform insoluble, glycosolated, have polypeptide chains >25,000 Daltons and are not essential for lung surfactant activity at the air: gas interface. The hydrophobic proteins, named SP-B and SP-C are not water soluble, are chloroform soluble, are not glycosolated, have polypeptide chains<26,000 Daltons after post translational modification to their active form, and are essential for normal biophysical and biologic activity of lung surfactant.

All of these surfactant proteins have been sequenced. The SP-C sequence has been determined in mice, dogs, rats, humans and cows and rats. The homology between the sequence of protein SP-C in humans and the sequence of protein SP-C in other species is >80%. The SP-B protein sequence has been determined for humans, dogs, rats, rabbits, mice and cows. Most of the sequence identity of SP-B is shared throughout species. (Whitsett J A and Baatz J E. Hydrophobic surfactant proteins SP-B and SP-C: molecular biology, structure and function in Robertson B, Van Golde L M G, Batenburg J J eds. *Pulmonary Surfactant: From Molecular Biology to Clinical Practice* Elsivier, New York, 1992, pp. 55–75.) Both SP-B and SP-C are synthesized initially as proproteins which comprise the active polypeptide chain plus additional amino acids added to one or both ends. After synthesis, the proproteins of SP-B and SP-C are modified by proteolytic processes to remove the additional amino acids, thereby yielding the active molecule. This process is referred to as post-translational modification.

Several forms of both the SP-B and SP-C active proteins are observed naturally. Monomers, single molecules, are observed as are oligomers or small numbers of chains bound together. Some oligomers are formed by sulfide bridges (ones that are broken into monomers by reducing agents) and some bound together by other, non-sulfide, bonds. Oligomers that are formed by sulfide bridges can be separated into monomers by reducing agents. It is unknown whether the proteins as synthesized or any intermediates have biologic activity. It is also unknown whether differences in activity exist between different oligomers, or between monomers and oligomers of these proteins.

Hydrophobic Proteins in Lung Surfactant Drugs

Eight different surfactants have been developed to treat newborn infants with Respiratory Distress Syndrome, RDS. Two lung surfactant drugs have lipids, but no surfactant proteins (Exosurf, ALEC). Three surfactant drugs have lipids and significant amounts of SP-C but low levels of SP-B (Survanta, Surfacten, Curosurf). Three others have significant amounts of both hydrophobic surfactant proteins (Infasurf, Alveofact, bLES). Infasurf and Alveofact are more biophysically active than Survanta or Curosurf, which in turn are more biophysically active than Exosurf. (Hall S B, Venkitaram A R, Whitsett J A, et al.: Importance of hydrophobic apoproteins as constituents of clinical exogenous surfactants. Am Rev Respir Dis 1992; 145:24–30; Seeger W., Grube C. Gunther A. Schmidt R. Surfactant inhibition by plasma proteins: differential sensitivity of various surfactant preparations, Eur Respir J 1993: 6:971–977.) Infasurf is more biologically active than Survanta, and Survanta is more biologically active than Exosurf, measured as either biophysical or physiologic activity. (Cummings J J, Holm B A, Hudak M L, Hudak B B, Ferguson W H, Egan E A: Controlled clinical comparison of four different surfactant preparations in surfactant-deficient preterm lambs. Am Rev Respir Dis 1991; 145:999–1003. Mizuno K, Ikegami M, Chen C M, Ueda T, Jobe A H. Surfactant protein-B supplementation improves in vivo function of a modified natural surfactant. *Pediatr Res* 1995; 37:271–276.) Clinically, Infasurf is more effective than Survanta or Exosurf, and Survanta is more effective than Exosurf. (Hudak M L, Farrell E E, Rosenberg A A et al. A multicenter randomized masked comparison trial of natural versus synthetic surfactant for the treatment of respiratory distress syndrome. *J Pediatr* 1996; 128:396–406; Bloom B T, Kattwinkel J, Hall R T et al. Comparison of Infasurf (calf lung surfactant extract) to Survanta (beractant) in the treatment and prevention of RDS. *Pediatrics* in Press, July 1997; Hudak M L, Cummings J J, Jung A L et al. Infasurf v. Exosurf for the prevention of neonatal respiratory distress syndrome: a multicenter randomized masked comparison trial. *Pediatrics* in press, July 1997.) The differences in activity of lung surfactants are associated with the amount and type of hydrophobic proteins they contain.

Preparation of Purified Hydrophobic Proteins

Surfactant proteins have been separated from surfactant lipids and SP-B has been separated from SP-C for academic investigations into protein metabolism and function. (Kogishi F, Kurozumi Y Fukite et al. Isolation and partial characterization of human low molecular weight protein associated with pulmonary surfactant. Am Rev Respir Dis 1988; 137:1426–1431; Mathialgian N, Possmayer F. Low molecular-weight hydrophobic proteins from pulmonary surfactant. *Biochem Biophys Acta* 1990: 1045:121–127; Takahshi A, Waring A J, Amirkhanian J, et al. Structure function relationships of bovine pulmonary surfactant proteins: SP-B and SP-C. *Biochim Biophys Acta* 1990, 1044:43–49; Wang Z, Gurel G, Baatz J E, Notter R H. Lung surfactant proteins SP-B and SP-C are not synergistic in surface active interactions with phospholipids *J. Lipid Res.* 1996; 37:1749–1760.) These methods describe organic extraction of natural surfactant followed by single or multiple column chromatography processes to separate hydrophobic proteins from lipids. Separation of the two hydrophobic surfactant proteins from each other has utilized repeated, additional column chromatography and/or preparative SDS PAGE, and/or reverse phase HPLC. Evaluation of the purity of the resulting proteins has been qualitative. Protein solutions produced by these methods have not reported yields. A process using only differential solubility in organic solvents has been described, but the method results in detectable levels of more than one polypeptide chain in the "pure" SP-B. (Beers M F, Bates S R, Fisher A B. Differential extraction for the rapid purification of bovine surfactant protein B. *Am J Physiol* 1992; 262:L773–L778.) None of these methods presents a practical method for securing significant quantities (milligrams or grams per procedure) of hydrophobic surfactant proteins, i.e., (1) a ≧50% yield of SP-B and/or SP-C from an amount of SP-B and/or SP-C in a reference sample or (2) SP-B and/or SP-C of ≧95% purity from biologically generated sources.

SUMMARY OF THE INVENTION

Definitions of Abbreviations

As used in this description, the following abbreviations have the following meanings:

ARDS—Adult (or Acute) Respiratory Distress Syndrome
° C.—degrees celsius
cm—centimeter
D—Dalton
DPPC—dipalmatoylphosphatidylcholine
g—gravity
>—greater than
$H_2O$—molecular abbreviation for water
HPLC—high pressure liquid chromatography
kD—kiloDalton
kg—kilogram
<—less than
l—liter
LPC—lysophosphatidylcholine
m—meter
μl—microliter
μm—micrometer (micron)
mg—milligram
min—minute
ml—milliliter
mm—millimeter
mM—milliMolar
mN—milliNewton
Ng—nanogram
N—Newton
$O_2$—molecular abbreviation for oxygen
PBS—pulsating bubble
PC—phosphatydilcholine
PC/DS—phosphatidylcholine—disaturated
PE—phosphatydilethanolamine
PG—phosophatidylglycerol
pH—negative logarithm of hydrogen ion concentration
PI—phosphatidylinositol
PL—phospholipid
RDS—Respiratory Distress Syndrome
rpm—revolutions per minute
SDS PAGE—sodium dodecylsulfate polyacrylimide gel electrophoresis
SP-A—surfactant protein A
SP-B—surfactant protein B
SP-C—surfactant protein C
SP-D—surfactant protein D
SPH—sphingomyelin
SN-1—position 1 of glycerol molecule
SN-2—position 2 of glycerol molecule
vol—volume

| Symbols for Amino Acids: | | |
|---|---|---|
| A | Ala | Alanine |
| B | Asx | Asparagine or aspartic acid |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |
| Z | Glx | Glutamine or glutamic acid |

New Compositions of Matter and Methods for Producing the Same

The invention is a new composition of matter which is a purified preparation of each of the SP-C and SP-B lung surfactant hydrophobic proteins which retain their full biophysical and physiologic activity. Each solution has ≧95% of peptides that are specific to a single protein by N-terminal amino acid sequencing, total amino acid analysis and SDS polyacrylamide gel electrophoresis. The new materials can be used to fabricate novel pharmacologic agents with specific SP-B and/or SP-C contents relative to other components.

According to another object of the present invention there is provided a method for separating hydrophobic proteins SP-B and SP-C from aqueous sources containing other biologic molecules.

According to another object of the present invention there is provided a method for separating hydrophobic proteins SP-B and SP-C from organic solvent solutions containing other biologic molecules.

According to another object of the present invention, there is provided a high-yield method for separating SP-B and SP-C from biological substances.

Other objects and advantages of the present invention will be apparent to those skilled in the art.

DESCRIPTION OF THE FIGURES

SDS PAGE of Reduced and Un-reduced SP-C

Lane 1=low molecular weight protein standards, 2.5, 6.2, 8.2, 14 and 17 kD.

Lane 2=10 ng of un-reduced purified SP-C. SP-C is present as a dimer in the ≈11 kD band and as a monomer in the ≈5 kD band. No other protein band is present.

Lane 3=high molecular weight protein standards, 14, 20, 24, 29, 36, 45 and 66 kD.

Lane 4=low molecular weight protein standards (see lane 1).

Lane 5=10 ng of purified SP-C with 5% mercaptoethanol to reduce disulfide bonds. Almost all the SP-C is now in the ≈5 kD band and only a faint trace remains un-reduced in the ≈11 kD band.

Lane 6=high molecular weight protein standards (see lane 3).

SDS PAGE of Reduced and Unreduced SP-B

Figure 2:
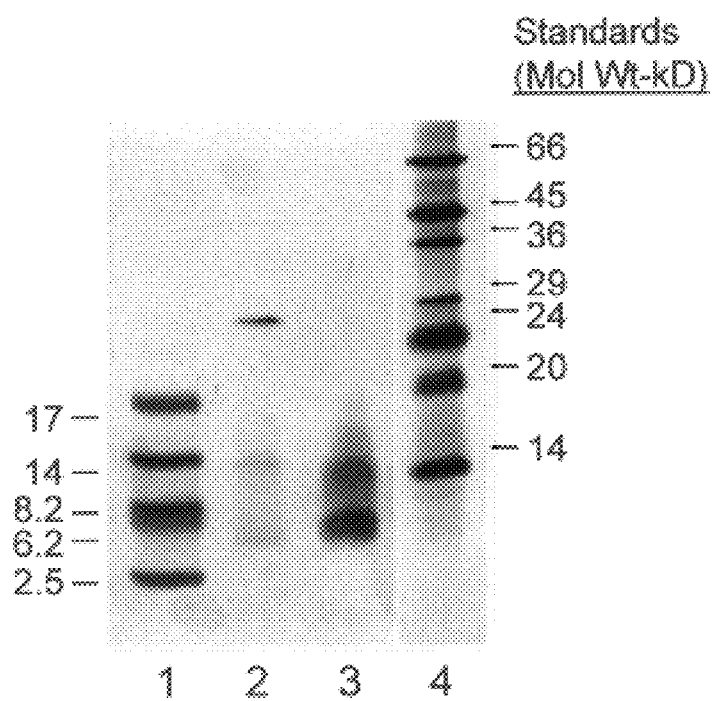

FIG. 2 shows a 20% continuous SDS polyacrylamide gel of purified surfactant protein SP-B run in Laemmli Buffer. All samples were applied at the top of the gel. Proteins were visualized using Coomassie Blue overlaid with a silver stain.

Lane 1=low molecular weight protein standards, 2.5, 6.2, 8.2, 14 and 17 kD.

Lane 2=25 ng of un-reduced purified SP-B. SP-B is present primarily as an oligomer in a single band at ≈26 kD. Small traces are seen in bands at ≈26 kD. Small traces are seen in bands at ≈14 kD and at ≈8 kD.

Lane 3=25 ng of purified SP-B with 5% mercaptoethanol to reduce disulfide bonds. All the SP-B is now in a ≈14 kD band and in a ≈8 kD band. The loss of definition of the bands is the result of overloading protein in the lane.

Lane 4=high molecular weight protein standards, 14, 20, 24, 29, 36, 45 and 66 kD.

Deflation Pressure Volume Curves in Excised Rat Lungs

Figure 3:
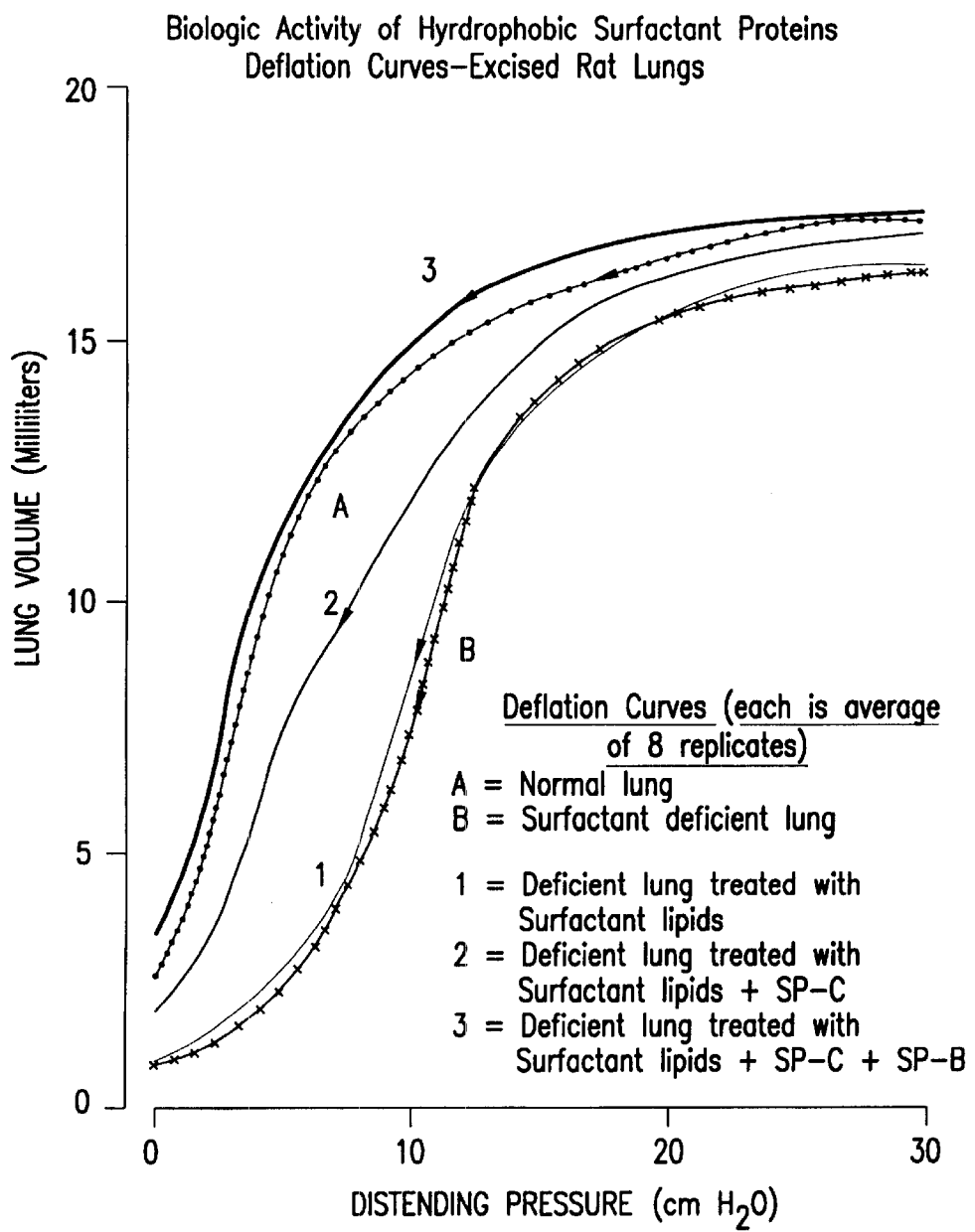

In FIG. 3, the volume of a freshly excised rat lung is plotted against the inflating pressure during a deflation cycle. Curve A is deflation in the normal excised lungs after removal from a rat; Curve B is deflation in lung surfactant deficient lungs after 20 rinses with 0.9% saline. Surfactant deficient lungs have higher surface tension in expiration and do not retain gas as well as normal lungs. In the region of the curve <20 cm $H_2O$ the volumes in the deficient lung are much less than those in the normal lung.

Curve 1 is deflation in surfactant deficient lungs treated by lung surfactant lipids without any protein and is statistically identical to untreated surfactant deficient lungs. Curve 2 is lung deflation in deficient lungs treated by (lung surfactant lipids +1% SP-C, wt/wt). Lungs treated with this mixture retain gas significantly better than deficient lungs, but still do not retain gas as well as normal lungs. Curve 3 is lung deflation in deficient lungs treated with (surfactant lipids+ 1% SP-C+0.75% SP-B, wt/wt/wt). When significant amounts of both hydrophobic proteins are combined with surfactant lipids lung deflation is restored to normal in surfactant deficient lungs.

DETAILED DESCRIPTION OF METHOD OF PREPARATION OF PURIFIED PROTEINS SP-B AND SP-C

Sources of Proteins SP-B and SP-C

There are several sources of biologically produced active surfactant proteins appropriate for purification.

(a) Natural lung surfactant recovered from alveoli by lavage of the lung lumen with aqueous solutions or organic solvents.

(b) Lung tissue minced and/or pulverized.

(c) Tissue or secretions from transgenic animals which express both the proteins and proteolytic enzymes required for post-translation modification of the pro-proteins so that active surfactant proteins are present in secretions (such as milk) or stored in tissues (such at fat).

(d) Active surfactant proteins produced by isolated cells of either eukaryotic or prokaryotic origin in which the genes for production and processing of these proteins are expressed.

(e) Active surfactant proteins which are produced by in vitro processing of proproteins of SP-B and SP-C produced by biological processes.

Initial Preparation of Source Material (a) If the source material is natural surfactant is recovered as a suspension in an aqueous liquid it is concentrated by centrifugal force.

(b) If the source material has surfactant proteins intermixed with biologic products other than, or in addition to, natural surfactant, the source material is homogenized in an aqueous solvent using physical processes and separated from the solvent by centrifugal force.

Separation of Hydrophobic and Hydrophilic Components

The concentrated source material is then separated into hydrophilic and hydrophobic components by adding it to 4 parts of an aqueous solvent containing halide salts (0. 15M NaCl, for example), and then sequentially mixing in (a) an organic solvent consisting of 5 parts non-polar solvent (chloroform, for example) and 10 parts polar organic solvent (methanol, for example), (b) another 5 parts of a non-polar organic solvent, (c) another 5 parts of the aqueous solvent, but without halide salts. (Bligh E G, Dyer W J. A rapid method of total lipid extraction and purification. *Canad J. Biochem Physiol* 1959; 37:911). After thorough mixing the liquids separate into a non-polar layer containing hydrophobic elements, an interfacial zone suspended material and a water:polar solvent phase. The non-polar solvent phase is retained for further proceeding.

Separation of Lipids from Hydrophobic Proteins

The hydrophobic elements dissolved in a non-polar organic solvent are now applied to a solid phase material for separation of molecules by size and hydrophobicity such as chromatography column or separation gels. If chromatography is used (such as LH columns, Pharmacia, Uppsala, Sweden) the column solvent is a non-polar organic solvent::polar organic solvent:acid mixture (chloroform:methanol:HCl, for example). If gels are used the hydrophobic components are recovered from the organic solvent by evaporation and dissolved in an appropriate buffer and solubilizing agent (0.1% SDS, 192 mM glycine, 25 mM Tris at pH 8.3, for example). From the eluate of the separation devices, fractions are chosen that contain high levels of proteins and low levels of phospholipids. The total phospholipid is measured by the method of Ames and protein by the method of Peterson. (Ames B N. Assay of inorganic phosphate, total phosphate and phosphatases. *Method Enzymol* 1966; 8:115–118; Peterson G. A simplification of the protein assay method of Lowry et al. which is more generally applicable *Analyt Biochem* 1977; 83:346–56.) The phospholipid:protein ratio is <1 (wt/wt) in every fraction appropriate for further processing.

Separation of SP-B from SP-C

If the hydrophobic proteins are dissolved in any buffer containing solvent, the buffers are removed by dialysis against the pure solvent. If the solvent in which the proteins are dissolved is not a non-polar:polar:acid mixture, the solvent is removed by evaporation under vacuum and heat and the proteins are re-dissolved in a non-polar:polar:acid mixture solvent (chloroform:methanol: 1N HCl, 47.5:47.5:5, vol/vol, for example). To this mixture add an aqueous solvent, (water in 33 parts, for example), polar organic solvent (methanol 47.5 parts, for example), polar organic solvent (chloroform 47.5 parts, for example), and aqueous solvent (water 47.5 parts, for example) are added sequentially. The mixture is allowed to separate into two phases, the organic solvent phase in which the SP-C is dissolved and the polar solvent:aqueous phase in which the SP-B is dissolved. The two phases are separated and the content of the protein assayed by the method of Peterson and the purity assayed by SDS PAGE.

EXAMPLES

Recovery from Biologic Milieu

Lung surfactant was harvested from the lungs of freshly slaughtered calves by securing a plastic tube in the trachea of 20 excised lungs, instilling 0.15M NaCl through the tube into the lumen of the lung until it was full and recovering the saline by applying suction. The procedure was then repeated on each lung. The recovered saline was then centrifuged at 14,000×G for 30 minutes at 5° C. The pellet was retained and the supernatant was discarded.

The pellet was recovered and suspended in 0.15 M saline to a total volume of 400 ml. The 400 ml was combined with 1.5 liter of 1:2 chloroform:methanol (vol/vol) and mixed by shaking. An additional 50 ml of chloroform was added and the mixed by shaking. Finally 500 ml of distilled water was added and mixed by shaking. The entire 2.4 liters was left to separate overnight at 4° C.

After 12 hours, the mixture had separated into a lower chloroform phase, an upper clear phase and an interphase of floccular material. Only the lower phase was recovered and the upper phase and interphase discarded. The chloroform was placed in a rotoevaporator and evaporated to dryness using vacuum and a water bath at 99° C. The residual material was resuspended in 100 ml of chloroform. Total phospholipid was assayed by the method of Ames and total protein by Peterson's modified Lowry method.

An aliquot containing approximately 600 mg of phospholipids and 12 mg of surfactant apoprotein was applied to a 80 cm lung 2.5 cm diameter LH 20 column using a chloroform:methanol: 1N HCl, 47.5:47.5:5, vol/vol solvent. After the void volume, the first 4 fractions of 2.0 ml each were collected and retained. Analysis of these fractions revealed they contained >60% of the protein applied to the column and that the phospholipid:protein ratio (wt/wt) in these fractions of the eluate was <1.

The 4 eluate fractions were pooled to contain 3.8 ml chloroform, 3.8 ml of methanol and 0.4 ml of 1N HCl. First 3.8 ml of methanol and 2.64 ml of water were mixed with the pooled eluates by shaking, then 3.8 ml of chloroform was added and mixed by shaking, and finally, 3.8 ml of water was added and mixed by shaking. The resultant mixture was centrifuged at 4,000×G for 15 minutes to separate the mixture into two phases, an upper methanol:water phase and slower chloroform phase. The upper phase was carefully aspirated off the lower phase and both phases were stored separately.

The upper phase was examined by SDS Page, N-terminal sequencing and amino acid analysis. SDS PAGE showed any SP-B (See FIG. 2). N-terminal sequencing and amino acid analysis was performed by AAI, an independent laboratory. A single polypeptide chain was detected whose N-terminus was:

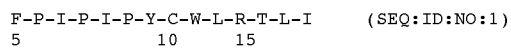

This sequence is identical to the sequence for the first 15 amino acids from the N-terminal region of bovine SP-B. (Olafson R W, Rink U, Kielland S, et al. Protein sequence analysis studies on the low molecular weight hydrophobic proteins associated with bovine pulmonary surfactant. *Biochem biophys Res Commun* 1987; 148:1406–1411.) Amino acid analysis used hydrolysis at 165° C. for 24 hours in 6N HCl with 1% phenol and was consistent with pure SP-B. The actual recovery of Leucine (L) was found to be 21% of all amino acids. Leucine is a well-recovered amino acid. If SP-C or another hydrophilic surfactant protein had been present at 5% or greater of the total amount of protein, the recovery of Leucine would have been less than 19% of all amino acids expected.

Figure 1:
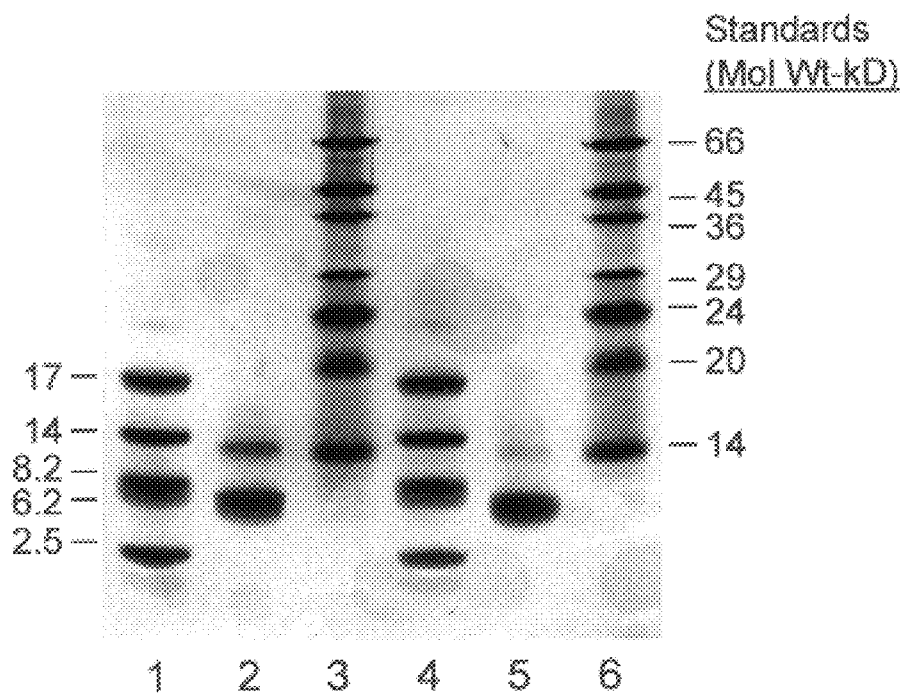
FIG. 1 shows a 20% continuous SDS polyacrylamide gel of purified surfactant protein SP-C run in Laemmli Buffer. All samples were applied at the top of the gel. Proteins were visualized using Coomassie Blue overlaid with a silver stain.

The lower, chloroform phase of the final extraction was also examined by SDS PAGE, N-terminal sequencing and amino acid analysis using the same methodologies as were used in analysis of the upper phase. SDS PAGE is shown in FIG. 1 and revealed only SP-C, and no SP-B. The N-terminal sequencing found a single polypeptide chain whose sequence was:

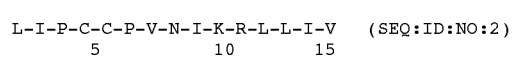

This sequence is identical to the one published by Olafson et al. for the N-terminal 15 amino acids of bovine SP-C. Amino acid analysis was consistent with pure SP-C. Complete digestion was not obtained, but none of the amino acids found in SP-B that are not found in SP-C (i.e., Q, T, Y, S, F, W, H, E, or D) were detected in significant amounts (≧2% of total amino acids) in the lower phase amino acids analysis.

The activity of both the purified SP-B and the purified SP-C proteins is demonstrated in FIG. 3. In FIG. 3, the volume of excised rat lungs during deflation is graphed as a function of the decreasing distending pressuring. Normal lungs are presented in Curve A and lung surfactant deficient lungs in Curve B. The deficient lungs retain much less volume at the same distending pressure than the normal lung once distending pressure fall below 20 cm H$_2$O. When surfactant lipids, without any protein are tested in deficient lungs (Curve 1) there is no improvement in deflation volume retention compared to the deficient lungs without any treatment. However, when the purified SP-C is added to surfactant lipids (Curve 2) there is improvement in the deflation volume retention, similar to that observed with SP-C containing, but SP-B deficient surfactant drugs like Survanta (Hall et al. op cit). If both purified SP-C and purified SP-B are added to surfactant lipids (Curve 3) the full deflation volume retention is restored to deficient lungs.

Uses for Separated and Purified SP-B and SP-C (a) Purified apoproteins can be used to investigate the specific biophysical and biological functions of the individual proteins.

(b) Increasing the amount of SP-B or SP-C can improve the function of some current lung surfactant drugs. Purified proteins can be used to increase the amount of hydrophobic proteins in such lung surfactant drugs.

(c) Purified proteins can be used to develop standards for specific Assays of SP-B and SP-C.

(d) Purified proteins can be used as is, or after modification, as functional elements in new products that benefit the health of humans and animals.

What is claimed:

1. A composition of matter, comprising:
   (a) a polypeptide having an amino acid sequence;
   (b) wherein the amino acid sequence of the polypeptide comprises the amino acid sequence of SP-C;
   (c) wherein the polypeptide comprises at least 95% of the composition.

2. A composition of matter, comprising:
   (a) a polypeptide having a biophysical activity;
   (b) wherein the biophysical activity of the polypeptide corresponds to the biophysical activity of SP-C;
   (c) wherein the polypeptide comprises at least 95% of the composition.

3. A composition of matter, comprising:
   (a) a polypeptide having a physiologic activity;
   (b) wherein the physiologic activity of the polypeptide corresponds to the physiological activity of SP-C;
   (c) wherein the polypeptide comprises at least 95% of the composition.

4. The composition of claim 1, 2 or 3 wherein the polypeptide is produced from an in vivo process.

5. The composition of claim 1, 2 or 3 wherein the polypeptide is produced from a pro-protein that is produced by an in vivo process.

6. A composition of matter, comprising:
   (a) a polypeptide having an amino acid sequence;
   (b) wherein the amino acid sequence of the polypeptide comprises the amino acid sequence of SP-C;
   (c) wherein the polypeptide comprises at least 70% of the composition;
   (d) wherein the composition is manufactured by a method in which the yield of the polypeptide from an amount of the polypeptide in a reference sample is at least 50%.

7. A composition of matter, comprising:
   (a) a polypeptide having a biophysical activity;
   (b) wherein the biophysical activity of the polypeptide corresponds to the biophysical activity of SP-C;
   (c) wherein the polypeptide comprises at least 70% of the composition;
   (d) wherein the composition is manufactured by a method in which the yield of the polypeptide from an amount of the polypeptide in a reference sample is at least 50%.

8. A composition of matter, comprising:
   (a) a polypeptide having a physiologic activity;
   (b) wherein the physiologic activity of the polypeptide corresponds to the physiologic activity of SP-C;
   (c) wherein the polypeptide comprises at least 70% of the composition;
   (d) wherein the composition is manufactured by a method in which the yield of the polypeptide from an amount of the polypeptide in a reference sample is at least 50%.

9. A composition of matter comprising the composition of claim 1, 2, 3, 6, 7 or 8.

10. The method of manufacturing the composition of claim 1, 2, or 3 wherein the yield of the polypeptide from an amount of the polypeptide in a reference sample is at least 50%.

11. The method of manufacturing a composition containing SP-B comprising the steps of:
    (a) obtaining a source material containing hydrophilic and hydrophobic surfactant components;
    (b) concentrating the source material;
    (c) separating the source material into hydrophilic components and hydrophobic components;
    (d) separating the hydrophobic components by size;
    (e) separating the hydrophobic components by hydrophobicity;
    (f) identifying hydrophobic components with a phospholipid:protein ratio <1;
    (g) separating the identified hydrophobic components into a fraction containing SP-B and a fraction containing SP-C.

12. The method of manufacturing a composition containing SP-C comprising the steps of:
    (a) obtaining a source material containing hydrophilic and hydrophobic surfactant components;
    (b) concentrating the source material;
    (c) separating the source material into hydrophilic components and hydrophobic components;

(d) separating the hydrophobic components by size;

(e) separating the hydrophobic components by hydrophobicity;

(f) identifying hydrophobic components with a phospholipid:protein ratio <1;

(g) separating the identified hydrophobic components into a fraction containing SP-B and a fraction containing SP-C.

13. The method according to claim 11 or 12 wherein the source material is natural lung surfactant recovered from alveoli by lavage of the lung lumen with aqueous solutions or organic solvents.

14. The method according to claim 11 or 12 wherein the source material is obtained from minced lung tissue.

15. The method according to claim 11 or 12 wherein the source material is obtained from pulverized lung tissue.

16. The method according to claim 11 or 12 wherein the source material is obtained from secretions from transgenic animals which express proteins and proteolytic enzymes required for post-translation modification of the pro-proteins.

17. The method according to claim 11 or 12 wherein the source material is obtained from tissue from transgenic animals which express proteins and proteolytic enzymes required for post-translation modification of the pro-proteins.

18. The method according to claim 11 or 12 wherein the source material is obtained from isolated cells.

19. The method according to claim 11 or 12 wherein the source material is obtained from in vitro processing of a pro-protein of SP-B.

20. The method according to claim 11 or 12 wherein the source material is obtained from in vitro processing of a pro-protein of SP-C.

21. The method according to claim 11 or 12 wherein the step of separating the source material into hydrophilic and hydrophobic components comprises the steps of:

(a) adding four (4) parts of an aqueous solvent containing halide salts;

(b) adding in five (5) parts of non-polar solvent;

(c) adding in ten (10) parts of polar organic solvent;

(d) adding in five (5) parts of an aqueous solvent;

(e) mixing the solvents; and (f) permitting the liquid to separate into a polar layer, a non-polar layer, and an interfacial layer.

22. The method according to claim 11 or 12 wherein the step of separating the identified hydrophobic components into a fraction containing SP-B and a fraction containing SP-C comprises the steps of:

(a) dissolving the hydrophobic components in a mixture containing a non-polar solvent, a polar solvent, and an acid;

(b) adding a first amount of an aqueous solvent;

(c) adding a polar organic solvent;

(d) adding a second amount of an aqueous solvent;

(e) permitting the mixture to separate into an organic solvent phase and polar solvent:aqueous phase.

* * * * *

SEQUENCE LISTING

<160> NUMBER OF SEQ ID NOS: 18

<210> SEQ ID NO 1
<211> LENGTH: 15
<212> TYPE: PRT
<213> ORGANISM: SP-B Peptide found in mammals

<400> SEQUENCE: 1

Phe Pro Ile Pro Ile Pro Tyr Cys Trp Leu Leu Arg Thr Leu Ile
 1               5                  10                  15

<210> SEQ ID NO 2
<211> LENGTH: 15
<212> TYPE: PRT
<213> ORGANISM: SP-C Peptide found in mammals

<400> SEQUENCE: 2

Leu Ile Pro Cys Cys Pro Val Asn Ile Lys Arg Leu Leu Ile Val
 1               5                  10                  15